United States Patent [19]

Parish

[11] Patent Number: 5,677,181

[45] Date of Patent: Oct. 14, 1997

[54] ANGIOGENESIS INHIBITORY ANTIBODIES

[75] Inventor: Christopher Richard Parish, Campbell, Australia

[73] Assignee: The Australian National University, Australia

[21] Appl. No.: 433,423

[22] PCT Filed: Oct. 29, 1993

[86] PCT No.: PCT/AU93/00558

§ 371 Date: Jul. 3, 1995

§ 102(e) Date: Jul. 3, 1995

[87] PCT Pub. No.: WO94/10331

PCT Pub. Date: May 11, 1994

[30] Foreign Application Priority Data

Oct. 29, 1992 [AU] Australia .................... PL5573

[51] Int. Cl.$^6$ ............... C12N 5/12; C07K 16/18
[52] U.S. Cl. ............... 435/332; 530/388.2; 530/389.1; 530/391.1; 530/391.3; 530/391.7
[58] Field of Search .............. 424/130.1, 152.1, 424/178.1, 181.1, 183.1; 530/387.1, 388.1, 391.3, 391.7, 389.1; 435/332

[56] References Cited

PUBLICATIONS

Hagemeier, Int. J. Cancer Res. 38:481–488, 1986.

Vitetta, Science 238:1098–1104, 1987.

Goldenberg et al. Ch. 13, in Immunoconjugates 1987 pp. 259–280 Oxford Univ. Press, NY.

Wang, Angigenesis EXS 61:266–271 Apr. 22, 1992.

Harris TIBTECH 11:42–44, 1993.

*Primary Examiner*—Lila Feisee
*Assistant Examiner*—Nancy A. Johnson
*Attorney, Agent, or Firm*—Fulwider Patton Lee & Utecht, LLP

[57] ABSTRACT

Antibodies, including monoclonal antibodies, specific for proliferating/angiogenic human endothelial cells such as human umbilical vein endothelial cells and human umbilical artery endothelial cells, and conjugates of these antibodies with a toxin material or label, are useful for inhibition of angiogenesis or for treatment of angiogenesis-dependent disease.

9 Claims, 1 Drawing Sheet

ANGIOGENESIS INHIBITORY ANTIBODIES

FIELD OF THE INVENTION

This invention relates to angiogenesis inhibitory antibodies, and to the use thereof in the inhibition of angiogenesis, particularly angiogenesis associated with the growth of solid tumours, with proliferative retinopathies, and with certain inflammatory diseases.

BACKGROUND TO THE INVENTION

The circulatory system represents an extensive, branching, network of blood vessels which is essential for the supply of oxygen and nutrients to tissues and for the removal of byproducts of metabolism. In adults the development of new blood vessels or "angiogenesis" rarely occurs except during wound healing or as a result of a number of pathological situations termed "angiogenesis-dependent diseases"[1,2]. The most important of these is the angiogenesis associated with the growth of solid tumours and with proliferative retinopathies. Angiogenesis may also play an important role in rheumatoid arthritis and psoriasis.

Angiogenesis inhibitors can, therefore, be of considerable value in the treatment of angiogenesis-dependent diseases. For example, in the case of solid tumours, the development of a blood supply is essential for the growth and survival of the tumour. Thus, inhibition of angiogenesis can provide a highly selective means of inducing tumour regression. Similarly, angiogenesis inhibitors may be used to prevent the blindness associated with proliferative diabetic retinopathy, one of the major complications of diabetes.

In work leading to the present invention, monoclonal antibodies (mAbs) have been developed against proliferating/angiogenic human endothelial cells which can be used either to directly inhibit angiogenesis or to target cytotoxic drugs or radioisotope labels to sites of angiogenesis. Since angiogenesis does not occur in adults, except following tissue injury, such mAbs can be remarkably specific. Furthermore, unlike other lines of research which have produced cancer cell-specific mAbs to target cytotoxic drugs to tumours, the present invention is directed to producing mAbs against host antigens. This approach has the major advantage that generation of "resistant" variants of the tumour cannot occur and, in theory, one mAb could be used to treat all solid tumours. An additional advantage is that endothelial cells, by virtue of their vascular location, are very accessible to mAbs in the circulation.

SUMMARY OF THE INVENTION

According to the present invention, there are provided antibodies, including monoclonal antibodies, specific for proliferating/angiogenic human endothelial cells. As used throughout the specification and claims, references to "proliferating" cells include "angiogenic" cells, and references to "non-proliferating" cells include "non-angiogenic" cells.

More particularly, the present invention provides antibodies, including monoclonal antibodies, specific for proliferating/angiogenic human umbilical vein endothelial cells (HUVEC) or human umbilical artery endothelial cells (HUAEC).

This invention also extends to hybridoma cell lines producing the monoclonal antibodies as described above, which may be produced by methods well known to persons skilled in this field.

As previously described, the antibodies in accordance with the invention may be used alone as an anti-angiogenesis agent in the treatment of angiogenesis-dependent disease in a patient.

In another aspect, the present invention provides an antibody-conjugate comprising an antibody specific for proliferating/angiogenic human endothelial cells, having a toxin material or label conjugated thereto.

The toxin material may, for example, be a cytotoxic drug or other cytotoxic material, however other toxin materials well known to persons skilled in this art may also be incorporated in the antibody-conjugate of this aspect of the invention. The label may be a radioisotope. Suitable toxin materials include, by way of example, ricin A chain, diphtheria toxin, Pseudomonas exotoxin A and idarubicin. A suitable radiolabel is technetium-99m. Coupling of various toxins to monoclonal antibodies may be effected by known methods[3,4,5,6,]. Similarly, the preparation of a conjugate with a radiolabel may use known method[7].

In yet another aspect, the invention provides a composition, particularly a therapeutic composition for inhibition of angiogenesis or for treatment of angiogenesis-dependent disease, comprising an antibody or antibody-conjugate as broadly described above, together with a pharmaceutically acceptable carrier or diluent.

The present invention also extends to a method for inhibition of angiogenesis in a patient, for example angiogenesis associated with the growth of solid tumours or with proliferative retinopathies, which comprises administration to said patient of an inhibition-effective amount of an antibody or antibody-conjugate as broadly described above.

In another aspect, this invention provides a method for treatment of angiogenesis-dependent disease in a patient, which comprises administration to said patient of a therapeutic-effective amount of an antibody or antibody-conjugate as broadly described above.

Administration of the antibody or antibody-conjugate may be by any suitable route. Preferably, the administration to the patient is parenterally, for example, by injection.

DETAILED DESCRIPTION OF THE INVENTION

In accordance with one embodiment of this invention, there have been developed monoclonal antibodies (mAbs) specific for proliferating/angiogenic endothelial cells. The major use of these mAbs is to simply inhibit angiogenesis, although if desired the mAbs can be used to target cytotoxic drugs or labels to angiogenic sites. In the case of tumours, this approach has the major advantages of tumour specificity, minimal side-effects, and little chance of "resistant" tumour variants arising. Furthermore, these mAbs provide a single therapeutic agent that can be used for all solid tumours, regardless of type and tissue location, and inhibition of angiogenesis in the solid tumours can result in tumour regression.

The initial experimental approach has been to raise murine mAbs against proliferating/angiogenic human umbilical vein endothelial cells (HUVEC). Resultant mAbs have been screened initially for HUVEC reactivity and, subsequently, mAbs have been eliminated which react with other human cell lines, e.g. human melanoma cell lines. Finally, endothelial specific mAbs have been identified which fail to react with freshly isolated, non-proliferating/non-angiogenic human endothelial cells. Using this approach, it has been clearly established that mAbs can be obtained which are specific for proliferating/angiogenic human endothelial cells.

Figure 1:
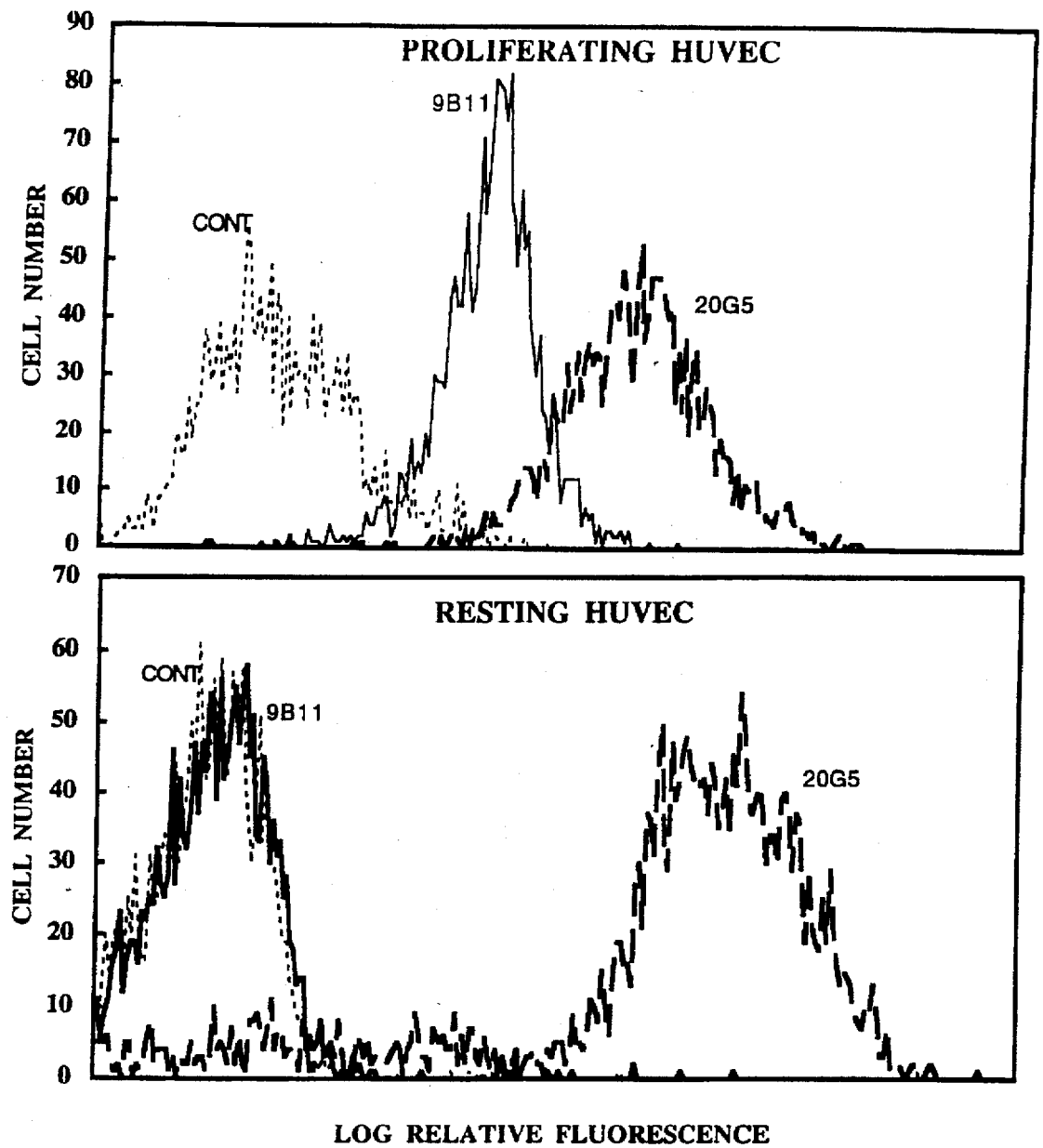
FIG. 1 shows binding of mAbs to proliferating/angiogenic and resting (non-proliferating/non-angiogenic) human umbilical vein endothelial cells (HUVEC) as detected by immunofluorescence flow cytometry. CONT refers to HUVEC not incubated with mAbs, 20G5 is a HUVEC-specific mAb which reacts with both proliferating/angiogenic and resting HUVEC and 9B11 is a HUVEC-specific mAb which only reacts with proliferating/angiogenic HUVEC.

Further details of the present invention will be apparent from the following detailed description of the production of endothelial specific mAbs in accordance with the invention.

EXAMPLE

A. Materials and Methods

Cells

Human umbilical vein (HUVEC) and artery (HUAEC) endothelial cells were prepared from human umbilical cords by the method of Jaffe[8] and cultured in Medium 199 supplemented with 20% foetal calf serum (FCS), L-glutamine, antibiotics, 130 ug/ml heparin and 1.2 mg/ml endothelial cell growth supplement (Sigma). HUVEC were used for mAb binding studies between passages 2 and 7 Human tumour cell lines (e.g. MM-170 melanoma, K562 erythroleukaemia) were cultured in RPMI-1640/10% FCS. Mononuclear cells (lymphocytes and monocytes) and neutrophils were simultaneously isolated from human peripheral blood by centrifugation of diluted blood on Polymorphprep™ (Nycomed. Pharma A.S., Oslo, Norway). Red cells and platelets were isolated by differential centrifugation from citrated human blood.

Production of Hybridomas

BALB/c mice were immunised, i.p., 3–4 times at 2–4 weekly intervals with $15 \times 10^6$ HUVEC in PBS and challenged 3 days prior to spleen cell removal with $15 \times 10^6$ HUVEC. A spleen cell suspension was prepared, fused with the myeloma NS1/1.AG4.1 and hybridomas grown up and cloned as described previously[9]. To improve hybridoma growth and cloning efficiencies 10% endothelial cell conditioned medium (HUVEC or bovine corneal EC) was included in culture media.

mAb Screening Assays.

Initially hybridoma culture supernatants were tested for reactivity with HUVEC by immunofluorescence fido cytometry. Briefly, HUVEC ($5 \times 10^4$) were incubated (30 min, 4° C.) with undiluted hybridoma supernatant, washed and incubated with FITC-sheep F(ab')$_2$ anti-mouse Ig(100 µg/ml). Following final washing HUVEC were examined for mAb binding by analysis on a Becton-Dickinson FACScan. Positive hybridoma supernatants were then screened on the human melanoma cell line MM-170 to eliminate non-endothelial specific mAbs. Endothelial specificity was further confirmed by screening mAbs on a panel of human tumour cell lines and human lymphocytes, monocytes, neutrophils, red cells and platelets. Finally, specificity for proliferating HUVEC was established by screening hybridoma supernatants on freshly isolated (non-cultured) HUVEC. Hybridomas which were positive on proliferating HUVEC but negative on freshly isolated HUVEC were cloned[9] for further study. A number of hybridomas (e.g. 20G5) which were endothelial-specific but not proliferation/angiogenesis-specific were also cloned.

HUVEC Proliferation Assay

Assays were performed in 96 well, flat bottom, microplates coated with 0.1% gelatin and containing $2.5 \times 10^4$ HUVEC/well in 150 µl of culture medium. After 24 hr culture cells were pulsed with $^3$H-thymidine for a further 24 hr and $^3$H-thymidine incorporation assessed in washed and harvested cells using a Titertek 530 cell harvester (Flow Labs). In mAb blocking experiments 50 µl/well of hybridoma supernatant was added at the commencement of the cultures with supernatant from a hybridoma which does not react with HUVEC being used as a negative control.

B. Results

Production of mAbs Specific for Proliferating/Angiogenic Endothelial Cells

Table 1 shows that mAbs can be obtained which are specific for proliferating/angiogenic human endothelial cells.

TABLE 1

Production of Endothelial Specific Monoclonal Antibodies (mAbs).

| | Number | |
|---|---|---|
| Hybridomas | Fusion #1 | Fusion #2 |
| Total screened | 1196 | 660 |
| Proliferating HUVEC positive | 811 | 276 |
| Proliferating HUVEC specific | 541[a] | 102[b] |
| Non-proliferating (resting) HUVEC negative | 25[c] | 17[c] |

[a]Hybridomas not reactive with the human melanoma cell line MM-170.
[b]Hybridomas not reactive with human MM170 cell line, U937 monocytic cell line, lymphocytes, neutrophils, monocytes, red cells and platelets.
[c]Hybridomas not reactive with endothelial cells freshly isolated from the human umbilical cord, i.e. endothelial cells "non-proliferating" or "resting".
HUVEC = Human umbilical vein endothelial cells.

In the first fusion of 1196 hybridomas screened, 811 reacted with proliferating/angiogenic endothelial cells of which 541 were proliferating/angiogenic endothelial cell specific, i.e. failed to react with other proliferating human cell lines such as the human melanoma line MM-170. Of particular importance was the fact that 25 of the 541 hybridomas specific for proliferating/angiogenic human endothelial cells failed to react with non-proliferating/non-angiogenic (freshly isolated) endothelial cells. Thus, 4.6% of hybridomas produce mAbs which are proliferation/angiogenesis specific, a clear validation of the approach being used. A similar result was obtained in a second fusion where 16.6% of the HUVEC-specific mAbs were angiogenesis specific. A typical example of the results obtained with a proliferation/angiogenesis-specific (9B11) and a proliferation/angiogenesis non-specific (20G5) mAb is depicted in FIG. 1 as revealed by immunofluorescence flow cytometry.

TABLE 2

Reactivity Pattern of Some Cloned Monoclonal Antibodies Against Human Endothelial Cells

| | mAb Clones | | | | | |
|---|---|---|---|---|---|---|
| Human Cells | 9D9 (IgM) | 12E5 (IgM) | 10A5 (IgM) | 14G11 (IgG1) | 21F10 (IgM) | 20G5 (IgM) |
| Proliferating HUVEC | + | + | + | + | + | + |
| Resting HUVEC | − | − | − | − | − | + |
| Proliferating HUAEC | + | + | + | + | + | |
| K562 erythroleukaemia | − | − | + | + | + | − |
| MM170 melanoma | − | ± | + | + | + | − |
| PE.01 ovarian carcinoma | − | − | + | + | + | − |
| COLO397 colonic carcinoma | − | − | + | + | + | − |
| KJD keratinocyte carcinoma | − | − | + | + | + | − |

TABLE 2-continued

Reactivity Pattern of Some Cloned Monoclonal Antibodies Against Human Endothelial Cells

| Human Cells | mAb Clones | | | | | |
|---|---|---|---|---|---|---|
| | 9D9 (IgM) | 12E5 (IgM) | 10A5 (IgM) | 14G11 (IgG1) | 21F10 (IgM) | 20G5 (IgM) |
| MT2 B lymphoma | − | − | + | + | + | + |
| Molt 4 T lymphoma | − | − | + | + | + | + |
| U937 (monocytic) | − | − | + | + | + | − |
| Lymphocytes | − | − | + | − | − | + |
| Neutrophils | − | ± | ± | − | − | + |
| Monocytes | − | + | + | ± | − | + |
| RBC | − | − | − | − | − | − |
| Platelets | ± | − | ± | + | − | + |
| Fibroblasts | − | − | + | ± | − | − |

HUVEC = human umbilical vein endothelial cells.
HUAEC = human umbilical artery endothelial cells.

Table 2 presents detailed specificity analysis of six cloned mAbs, which were HUVEC reactive, as examples. One mAb (20G5) is a control which reacts with both resting and proliferating/angiogenic endothelial cells and is probably specific for the CD31 antigen. The remaining five mAbs react with proliferating/angiogenic but not resting endothelial cells. Three of these mAbs (10A5, 14G11, 21F10) react with many other proliferating cell types. The remaining two clones (9D9 and 12E5) exhibit considerable specificity for proliferating/angiogenic endothelial cells, 9D9 being the mAb with the greatest specificity, only exhibiting a weak reaction with platelets.

The 9D9 mAb reacts with proliferating/angiogenic venular or arterial endothelial cells but not non-proliferating (resting) endothelial cells (Table 2). Subsequent studies showed that the 9D9 antigen appears on cultured HUVECS within 24 hr of culture and persists on HUVEC cultured for many passages, i.e. ten passages over a period of two months. The 9D9 antigen also appears on HUVEC whether they are cultured in 20% FCS+bovine growth supplement or 20% human serum, indicating that the 9D9 antigen is not derived from culture medium components.

Effect of mAbs on Endothelial Cell Proliferation.

When some of the proliferation-specific mAbs were added to proliferating HUVEC in vitro it was found that some of the mAbs could directly inhibit HUVEC proliferation. The results of a typical experiment are present in Table 3.

TABLE 3

Inhibition of HUVEC Proliferation by mAbs Specific for Proliferating/Angiogenic Endothelial Cells.

| mAb | Specificity | $^3$H-Thymidine Incorporation* (cpm) | Response % Control |
|---|---|---|---|
| 9B9 | Non-reactive | 7779 ± 1420 | 100 |
| 20G5 | HUVEC | 6806 ± 1290 | 87.5 |
| 1D5 | Proliferating HUVEC** | 1256 ± 110 | 16.1 |
| 8G4 | Proliferating HUVEC** | 1857 ± 38 | 23.9 |
| 16C6 | Proliferating HUVEC** | 1767 ± 175 | 22.7 |
| 19D4 | Proliferating HUVEC** | 7530 ± 753 | 96.8 |

*HUVEC cultured in proliferation assay with dialyzed hybridoma supernatants containing mAbs. Proliferation measured 24–48 hr following culture initiation and represents mean ± standard error of three determinations.
**mAbs only react with proliferating/angiogenic (not resting) HUVEC.

Of the four proliferation/angiogenesis-specific mAbs tested, three (1 D5, 8G4 and 16C6) inhibited HUVEC proliferation by approx. 75–85% as measured by $^3$H-thymidine incorporation. In contrast, one proliferation/angiogenesis-specific mAb (19D4) and 20G5, a mAb which reacts with both proliferating and non-proliferating HUVEC, had no significant effect on HUVEC proliferation. The mAb 9B9, which does not react with HUVEC, was used as the negative control in this experiment.

These data strongly suggest that some of the proliferation/angiogenesis-specific mAbs may directly inhibit angiogenesis, thus bypassing the need for cytotoxic drug-mAb conjugates. It should be emphasised that the data presented in Table 2 were obtained with hybridoma supernatants and not with purified and concentrated mAb preparations.

REFERENCES

1. Folkman, J. *Adv. Cancer Res.* 43, 175–203 (1985).
2. Folkman, J. and Klagsbrun, M. *Science* 235, 442–447 (1987).
3. Bridges, S., Longo, D. L. and Youle, R. J. *Methods Enzymol.* 178, 356–368 (1989).
4. Colombatti, M., Dell'Arciprete, L., Rappouli, R. and Tridente, G. *Methods Enzymol.* 178, 404–422 (1989).
5. Kondo, T., Fitzgerald, D., Chaudhary, V. K., Adhya, S. and Pastan, I. *J.Biol.Chem.* 263, 9470–9475 (1988).
6. Pietersz, G. A., Smyth, M. J. and McKenzie, I. F. C. *Cancer Res.* 48, 926–931 (1988).
7. Lee, R-T., Milner, L. J., Boniface, G. R., Bautovich, G. J., Weedon, A. R. J., Bundesen, P. G., Rylatt, D. B. and Walker, K. Z. *Immunol. Cell Biol.* 70, 173–179 (1992).
8. Jaffe, E. A. In "*Biology of Endothelial Cells*", E. A. Jaffe, ed., Martinus-Nijhoff, The Hague (1984).
9. Goding, J. W. *J. Immunol. Methods* 39, 285–308 (1980).

I claim:

1. An antibody which specifically binds proliferating human endothelial cells, said antibody binding proliferating human endothelial cells selected from the group consisting of proliferating human umbilical vein endothelial (HUVE) cells and human umbilical artery endothelial (HUAE) cells and not binding cells selected from the group consisting of non-proliferating HUVE cells and non-proliferating HUAE cells.

2. An antibody according to claim 1 which is a monoclonal antibody.

3. A hybridoma cell line producing a monoclonal antibody according to claim 2.

4. An antibody-conjugate comprising an antibody according to claim 1, having a toxin material or detectable label conjugated thereto.

5. An antibody-conjugate according to claim 4 wherein said antibody is a monoclonal antibody.

6. An antibody-conjugate according to claim 4, wherein said antibody is conjugated to a cytotoxic material.

7. An antibody-conjugate according to claim 6, wherein said cytotoxic material is ricin A chain, diphtheria toxin, Pseudomonas exotoxin A or idarubicin.

8. An antibody-conjugate according to claim 4, wherein said antibody is conjugated to a radioisotope label.

9. An antibody-conjugate according to claim 8, wherein said radioisotope label is technetium-99m.

* * * * *

UNITED STATES PATENT AND TRADEMARK OFFICE
CERTIFICATE OF CORRECTION

PATENT NO. : 5,677,181
DATED : Oct. 14, 1997
INVENTOR(S) : Christopher Richard Parish It is certified that error appears in the above-identified patent and that said Letters Patent is hereby corrected as shown below:

Column 4, "TABLE 2", Line 60, under "20G5" for row "Proliferating HUAEC", add -- + -- to that column.

Signed and Sealed this

Nineteenth Day of May, 1998

BRUCE LEHMAN

*Attest:*

*Attesting Officer*     Commissioner of Patents and Trademarks

(12) EX PARTE REEXAMINATION CERTIFICATE (6650th)
United States Patent
Parish

(10) Number: US 5,677,181 C1
(45) Certificate Issued: Feb. 10, 2009

(54) ANGIOGENESIS INHIBITORY ANTIBODIES

(75) Inventor: Christopher Richard Parish, Campbell (AU)

(73) Assignee: The Australian National University, Acton, Australian Capital Territory (AU)

Reexamination Request:
No. 90/008,673, Jul. 11, 2007

Reexamination Certificate for:
Patent No.: 5,677,181
Issued: Oct. 14, 1997
Appl. No.: 08/433,423
Filed: Jul. 3, 1995

Certificate of Correction issued May 19, 1998.

(22) PCT Filed: Oct. 29, 1993

(86) PCT No.: PCT/AU93/00558
§ 371 (c)(1),
(2), (4) Date: Jul. 3, 1995

(87) PCT Pub. No.: WO94/10331
PCT Pub. Date: May 11, 1994

(51) Int. Cl.
*A61K 38/00* (2006.01)
*A61K 47/48* (2006.01)
*C07K 16/28* (2006.01)
*C07K 16/18* (2006.01)

(52) U.S. Cl. .................. 435/332; 435/388.2; 435/389.1; 435/391.1; 435/391.3; 435/391.7

(58) Field of Classification Search ....................... None
See application file for complete search history.

(56) References Cited

FOREIGN PATENT DOCUMENTS

WO WO-89/05155 6/1989

OTHER PUBLICATIONS

Clarke, Mark S. F. et al., "The identification of proliferation and tumour–induced proteins in human endothelial cells: A possible target for tumour therapy," Electrophoresis, 1991, vol. 12, pp. 500–508.
Denekamp, J., "Endothelial cell proliferation as a novel approach to targeting tumour therapy," BR. J. Cancer, 1982, vol. 45, pp. 136–139.
Barrett, Thomas B. et al., "Expression of the sis gene by endothelial cells in culture and in vivo," Proc. Natl. Acad. Sci., USA, 1984, vol. 81, pp. 6772–6774.
Houghton, Alan N. et al., "Monoclonal antibodies: potential applications to the treatment of cancer," Seminars in Oncology, 1986, vol. 13, pp. 165–179.

*Primary Examiner*—Padmashri Ponnaluri

(57) ABSTRACT

Antibodies, including monoclonal antibodies, specific for proliferating/angiogenic human endothelial cells such as human umbilical vein endothelial cells and human umbilical artery endothelial cells, and conjugates of these antibodies with a toxin material or label, are useful for inhibition of angiogenesis or for treatment of angiogenesis-dependent disease.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–9 is confirmed.

* * * * *